United States Patent [19]

Franz et al.

[11] Patent Number: 4,592,412

[45] Date of Patent: Jun. 3, 1986

[54] METHOD OF PERIODICALLY HEATING A PRODUCT SEPARATOR OF A PLANT FOR PRODUCING PHTHALIC ANHYDRIDE OR MALEIC ANHYDRIDE

[75] Inventors: Volker Franz; Rolf Geissen, both of Frankfurt am Main, Fed. Rep. of Germany

[73] Assignee: Metallgesellschaft Aktiengesellschaft, Frankfurt am Main, Fed. Rep. of Germany

[21] Appl. No.: 711,915

[22] Filed: Mar. 14, 1985

[30] Foreign Application Priority Data

Mar. 30, 1984 [DE] Fed. Rep. of Germany ....... 3411732

[51] Int. Cl.⁴ ............................................. F25B 29/00
[52] U.S. Cl. ......................................... 165/2; 165/61; 165/64; 23/294 R; 422/244; 237/67
[58] Field of Search ............... 165/61, 2, 64; 422/244; 23/294 R, 294 S; 237/67; 55/269

[56] References Cited

U.S. PATENT DOCUMENTS 2,961,301 11/1960 Steinhoff ........................... 422/244
4,252,772 2/1981 Way .................................. 422/244

FOREIGN PATENT DOCUMENTS 35173 9/1981 European Pat. Off. ............ 422/244

Primary Examiner—Albert W. Davis, Jr.
Attorney, Agent, or Firm—Sprung, Horn, Kramer & Woods

[57] ABSTRACT

In a method of periodically heating a product separator of a plant for producing anhydride or maleic anhydride, a PA or MA product is deposited on cooling surfaces of the product separator. To melt the product, the cooling surfaces are indirectly heated by means of a heated liquid, which is circulated through the product separator. The liquid heat transfer medium is indirectly heated with steam in a heater for the heat transfer medium. At least during the time of the largest steam demand, most of that steam is taken from a steam accumulator, which is charged with steam supplied from the plant for producing PA or MA. The charging of the steam accumulator is effected to at least a substantial degree during the time in which the heater for the heat transfer medium is out of operation or is operated under a low load.

6 Claims, 2 Drawing Figures

METHOD OF PERIODICALLY HEATING A PRODUCT SEPARATOR OF A PLANT FOR PRODUCING PHTHALIC ANHYDRIDE OR MALEIC ANHYDRIDE

BACKGROUND OF THE INVENTION

The present invention relates to a method of periodically heating a product separator of a plant for producing phthalic anhydride (PA) or maleic anhydride (MA), wherein a liquid heat transfer medium is indirectly heated by means of steam in a heat exchanger (heater for the heat transfer medium) and the liquid medium is circulated through the product separator to indirectly heat and melt the PA or MA product deposited on cooling surfaces.

In the conventional separation of the raw PA or MA product, the gas coming from the producing plant is cooled and the product is deposited mainly by desublimation on the outside of an indirectly cooled heat exchanger. The deposited raw product is discharged after it has been melted. The liquid heat transfer medium is mostly the same as that used in the cooling phase and usually consists of heat transfer oil and is conducted through the heat exchanger at a temperature which exceeds the melting temperature of the product. Outside the product separator the liquid heat transfer medium is reheated in the heater for the heat transfer medium; that heater is heated with steam. A method of that kind has been described in European Patent Specification No. 35 173. In that known method the strong fluctuations of the heat demand are compensated in that the liquid heat transfer medium is conducted through a heating circuit, which includes a reservoir, and liquid heat transfer medium is periodically taken from that reservoir.

SUMMARY OF THE INVENTION

It is an object of the invention to compensate the fluctuations of the heat demand in a manner which is as simple and as economical as possible.

In the method described first hereinbefore, that object is accomplished in that most of the steam used to indirectly heat the liquid heat transfer medium is taken from a steam accumulator at least during the time of the largest steam demand and the accumulator is charged with steam supplied from the plant for producing PA or MA. The rate at which steam is produced in the overall plant usually exceeds the total rate at which steam is consumed in that plant so that surplus steam at a certain rate is always available and can be used for other purposes. In that connection it is important that the fluctuations of the rate at which steam is delivered to the outside should be minimized because the adaption of the consumers to such fluctuations is difficult and steam can be economically used only at that rate which is always available.

Owing to the provision of the steam accumulator in accordance with the invention, the rate at which steam is withdrawn from the plant for producing PA or MA can be kept constant with a variation not in excess of $\pm 5\%$ and usually not in excess of $\pm 2\%$ so that steam is available for other consumers at a substantially constant rate.

The steam accumulator is a known unit, in which hot water is maintained under pressure so that steam at a desired rate can be taken as a result of a controlled pressure relief. In the method in accordance with the invention, the pressure in the steam accumulator varies in most cases in the range from about 3 to about 40 bars. Because the melting temperature of the PA or MA product is much lower than the boiling temperature in the steam accumulator when it is fully charged, a major part of the heat required for heating and melting can be supplied to the heater for the heat transfer medium at a relatively low temperature so that the accumulator will have a small volume per unit of heat storage capacity and its container will have small dimensions.

Another advantage afforded by the method resides in the fact that the liquid heat transfer medium is heated only to relatively low temperatures so that low-cost mineral oils can be used too.

A possible embodiment of the method will be explained with reference to the drawing, wherein:

DETAILED DESCRIPTION OF THE INVENTION

A reactor 1 for producing PA is supplied through line 2 with mixed feedstocks consisting of air from line 3 and orthoxylene ornaphthalene from line 4. The feedstocks for the production of MA are air and benzene or low-boiling hydrocarbons ($C_4$ cut). Such synthesis processes are known and need not be described here more in detail. The highly exothermic reaction in the reactor 1 is indirectly cooled by means of molten salt, which enters the reactor from line 5 and leaves the reactor in line 6. The molten salt is cooled in the heat exchanger 7 by means of feed water from line 8 and the resulting steam is withdrawn in line 9.

The gas produced by the reaction consists of a mixture of product (PA or MA) vapor and air and leaves the reactor 1 in line 10 and is subjected to a first indirect cooling in a cooler 11, which is also supplied with feed water. The resulting steam can also be delivered to the line 9. Precooled gas produced by the reaction is supplied in line 12 to the separator 13, in which the product is cooled further and solidified.

Figure 1:
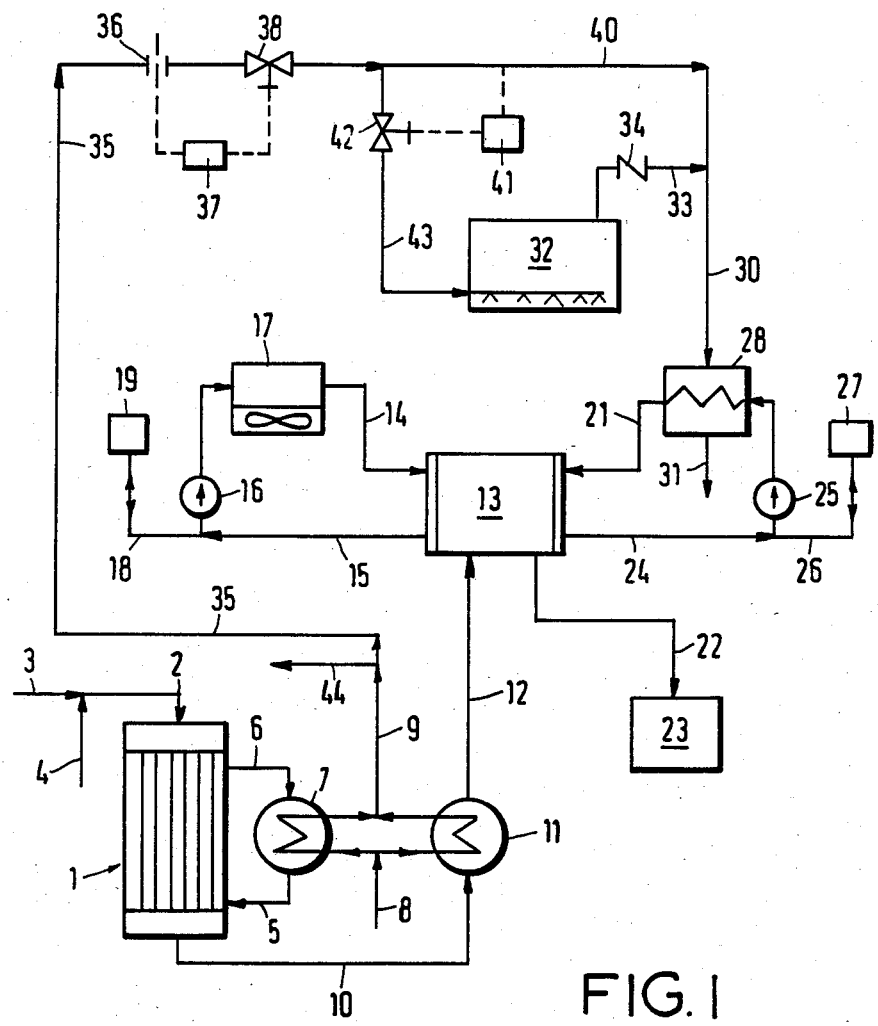
FIG. 1 is a diagramatic representation of the process.

One reactor 1 has usually at least three separators 13 associated with it and product-containing gas produced by the reaction is supplied from line 12 to said separators in a cyclical sequence. For the sake of simplicity, only a single separator is shown in FIG. 1. A cooling of the separator 13 and a deposition of the product on the cooling surfaces are effected by a liquid coolant, which is supplied in line 14 and leaves the separator 13 in line 15. The liquid coolant is circulated by a circulating pump 16 through a cooler 17. The circuit for the circulation of the liquid coolant is connected by a tap line 18 to an expansion vessel 19. The temperature of the liquid coolant is usually in the range from 45° to 60° C. in the line 14 and in the range from 50° to 70° C. in the line 15.

The liquid coolant preferably consists of an oil, which is used also as a liquid heat transfer medium for heating the separator 13 and for melting the deposited product. During the heating phase, the supply of gas produced by the reaction from line 12 to the separator 13 is interrupted and that gas is then supplied to other separators, not shown. The supply of liquid coolant is also discontinued at that time.

Liquid heat transfer medium at a temperature of 140° to 210° C. now flows from line 21 into the separator 13 and causes the deposited product in the separator to melt, whereafter the product flows through line 22 into a tank 23. The circuit for the circulation of the liquid for heating the separator 13 includes the return line 24, the circulating pump 25 incorporated therein, the tap line 26 and the expansion vessel 27. The temperature of the liquid in line 24 is usually in the range from 100° to 200° C. The liquid heat transfer medium usually consisting of an oil is indirectly heated in the heater 28 for the heat transfer medium by means of steam from line 30. Cooled steam and condensate leave the heater 28 through line 31.

At the beginning of the heating in the separator 13 there is a large heat demand in the heater 28 and a major part of the required steam is taken from the steam accumulator 32 and flows through line 33, which contains a check valve 34, and through line 30 to the heater 28.

Steam at a constant rate is supplied in line 35. The constant flow rate is monitored by a flow meter 36 and maintained by means of a controller 37 and a flow control valve 38. The pressure in line 35 is usually in the range from about 15 to about 40 bars. During the first portion of the heating operation the steam consumption in the heater 28 is large and the pressure therein is correspondingly low. At that time, steam from line 35 flows into line 40 and mixes with the steam delivered in line 33 from the steam accumulator 32. Toward the end of the heating operation the consumption of steam has decreased and the pressure in the heater 28 has increased. As a result, a pressure controller 41 opens the flow control valve 42, which is incorporated in the line 43 leading to the steam accumulator 32, and the accumulator 32 is then charged.

As soon as the rate at which steam is condensed in the heater 28 exceeds the rate at which steam is supplied from line 40, the pressure on the steam side of the heater rises and steam is no longer taken from the steam accumulator 32. The pressure-controlled flow control valve 42 and the check valve 34 initially prevent a flow of the continuously supplied steam into the accumulator. As a result, the steam pressure in the heater 28 rises to its maximum within a short time, as is desired. Only when that maximum has been reached and the rate of the inflowing steam supply rate exceeds the rate required at that point, is the flow control valve 42 opened to such an extent that the steam pressure in the heater 28 is maintained. The surplus steam rate now flows through line 43 into the accumulator 32 and heats the same so that the pressure rises continuously.

When the melting operation in the separator 13 has been terminated, the separator is connected to the cooling circuit (lines 14 and 15, pump 16 and cooler 17) and is then recooled. The steam consumption in the heater 28 for the heat transfer medium decreases almost to zero and almost all inflowing steam is received by the accumulator 32 until the same pressure has been reached throughout the system downstream of the line 35.

The equipment required for the separation of the product consists of a steam accumulator 32 and a heater 28 and a plurality of separators 13 operated in a cyclical sequence.

Figure 2:
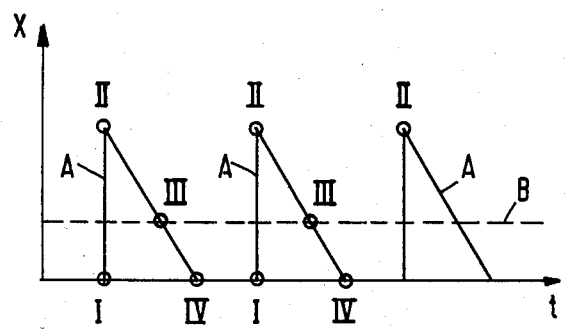
FIG. 2 is a graph in which the steam consumption is compared.

In the graph of FIG. 2, the change of the steam consumption X in the heater 28 is represented by a sawtooth line A and the constant rate at which steam is supplied in line 35 is represented by a dotted line B. The interposed steam accumulator 32 permits the use of steam supplied at a constant rate in spite of the strong consumption peaks apparent from line A. Because only part of the steam conducted in line 9 is forwarded in line 35, steam at a constant rate can be supplied to other consumers in line 44.

If at least three separators are used, as is usual, said three sawtooth peaks shown in FIG. 2 will be associated with respective separators.

One of the separators 13 is connected to initiate the melting operation therein at the time I. Steam at the maximum rate is consumed in the heater 28 at the closely succeeding time II. There is no longer a need for a delivery of steam from the steam accumulator 32 at the time III and the pressure in the accumulator and in the heater 28 has reached a minimum at that time. The heating of the separator which has performed the melting operation is discontinued at the time IV.

EXAMPLE

A system as shown in FIG. 1 is operated as follows:

A mixture of raw PA vapor and air leaves the reactor 1 through line 10 at a rate of 81,000 kg/h and at a temperature of 380° C. The mixture is subjected to a preliminary cooling in the cooler 11 and at a temperature of 170° flows into one of four separators 13. Owing to the dissipation of heat in the cooler 11 and the heat exchanger 7, steam consisting of saturated steam at 20 bars can be conducted in line 9 at a rate of 24,000 kg/h. 10% (2400 kg/h) of that saturated steam are supplied through line 35 into the heater 28 and/or the steam accumulator 32. The remaining saturated steam is delivered to other consumers in line 44.

The separators are cooled and heated by means of a conventional heat transfer oil, which consists of a mineral oil. That oil flows through line 14 or 21 at a rate of 110,000 kg/h. Because the heat required to melt the product in a given separator varies with time, the flow rate of the oil varies too, as is apparent from the following Table. It designates the time immediately before the beginning of the heating of the separator. There is an interval of about 2 hours between consecutive times I, see FIG. 2 of the drawing. The times designated II, III and IV have the meanings explained hereinbefore with reference to FIG. 2. P designates the pressure, Q the flow rate, and T the temperature in the designated line. The pressure in lines 33 and 30 equals the pressure in line 40.

TABLE

| Line | | Time | | | |
|---|---|---|---|---|---|
| | | I | II | III | IV |
| 40 | P (bars) | 19 | 18 | 6 | 19 |
| | Q (kg/h) | 100 | 2400 | 2400 | 100 |
| 33 | Q (kg/h) | — | 5600 | — | — |
| 43 | P (bars) | 18 | 18 | 6 | 8 |
| | Q (kg/h) | 2300 | — | — | 2300 |
| 30 | Q (kg/h) | 100 | 8000 | 2400 | 100 |
| 14 | T (°C.) | 55 | — | — | — |
| 15 | T (°C.) | 70 | — | — | — |
| 21 | T (°C.) | — | 140 | 150 | 150 |
| 24 | T (°C.) | — | 100 | 135 | 185 |

Time difference II − I is about 2 minutes, III − I is about 35 minutes and IV − I is about 1 hour.

What is claimed is:

1. In a method of periodically heating a product separator of a plant for producing phthalic anhydride (PA) or maleic anhydride (MA), wherein a liquid heat transfer medium is indirectly heated by means of steam in a heat exchanger and the liquid medium is circulated through the product separator to indirectly heat and melt the PA or MA product deposited on cooling surfaces, the improvement comprising obtaining most of the steam used to indirectly heat the liquid heat transfer medium from a steam accumulator at least during the time of the largest steam demand and charging the accumulator with steam supplied from the plant for producing PA or MA.

2. The method according to claim 1, wherein the charging of the steam accumulator is effected at least to a large extent during the interval of time in which the heater for the heat transfer medium is out of operation or operated under a low load.

3. The method according to claim 1, wherein the pressure in the steam accumulator varies within the range from about 3 bars to about 40 bars.

4. The method according to claim 1, wherein the rate at which steam is supplied from the plant for producing PA or MA is maintained constant with a variation not in excess of ±5%.

5. The method according to claim 1, wherein the steam supplied from the plant for producing PA or MA is supplied directly to the heater for the heat transfer medium at the beginning of the operation to melt the product.

6. The method according to claim 1, wherein the charging of the steam accumulator is inititated after the maximum pressure has been reached in the heater for the heat transfer medium.

* * * * *